(12) United States Patent
Vince et al.

(10) Patent No.: US 7,175,597 B2
(45) Date of Patent: Feb. 13, 2007

(54) NON-INVASIVE TISSUE CHARACTERIZATION SYSTEM AND METHOD

(75) Inventors: D. Geoffrey Vince, Avon Lake, OH (US); Anuja Nair, Cleveland Heights, OH (US); Jon D. Klingensmith, Shaker Heights, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 107 days.

(21) Appl. No.: 10/356,812

(22) Filed: Feb. 3, 2003

(65) Prior Publication Data

US 2004/0152983 A1 Aug. 5, 2004

(51) Int. Cl.
*A61B 8/00* (2006.01)
(52) U.S. Cl. ...................................... 600/443
(58) Field of Classification Search ................ 600/437, 600/440–447, 449–450, 459, 466–467; 128/916; 382/128
See application file for complete search history.

(56) References Cited

U.S. PATENT DOCUMENTS

| | | | |
|---|---|---|---|
| 4,063,549 A * | 12/1977 | Beretsky et al. | 600/443 |
| 4,945,478 A * | 7/1990 | Merickel et al. | 382/131 |
| 5,003,579 A * | 3/1991 | Jones | 379/93.05 |
| 5,417,215 A * | 5/1995 | Evans et al. | 600/442 |
| 6,132,373 A | 10/2000 | Ito et al. | |
| 6,165,128 A * | 12/2000 | Cespedes et al. | 600/463 |
| 6,200,268 B1 | 3/2001 | Vince et al. | |
| 6,264,609 B1 * | 7/2001 | Herrington et al. | 600/443 |
| 6,381,350 B1 | 4/2002 | Klingensmith et al. | |
| 6,415,046 B1 * | 7/2002 | Kerut, Sr. | 382/128 |
| 6,585,647 B1 * | 7/2003 | Winder | 600/437 |
| 6,730,035 B2 * | 5/2004 | Stein | 600/449 |
| 6,776,760 B2 * | 8/2004 | Marmarelis | 600/448 |
| 6,816,743 B2 * | 11/2004 | Moreno et al. | 600/473 |
| 6,817,982 B2 * | 11/2004 | Fritz et al. | 600/443 |
| 6,835,177 B2 * | 12/2004 | Fritz et al. | 600/443 |
| 2003/0220556 A1 * | 11/2003 | Porat et al. | 600/407 |
| 2004/0122326 A1 * | 6/2004 | Nair et al. | 600/467 |

OTHER PUBLICATIONS

Comparison of texture analysis methods for the characterization of coronary plaques in intravascular ultrasound images; Vince, et al., Computerized Medical Imaging and Graphics, 2000, vol. 24, pp. 221-229.
Assessment of coronary compensatory enlargement by three-dimensional intravascular ultrasound; Klingensmith et al., International Journal of Cardiac Imaging, 2000, vol. 16, pp. 87-98.
Assessing spectral algorithms to predict atherosclerotic plaque composition with normalized and raw intravascular ultrasound data; Nair et al., Ultrasound In Medicine & Biology, 2001, vol. 27, No. 10, pp. 1319-1331.
International Search Report from the International Searching Authority in connection with PCT Patent Application PCT/US04/02367.

* cited by examiner

*Primary Examiner*—Francis J. Jaworski
(74) *Attorney, Agent, or Firm*—Benesch, Friedlander, Coplan & Aronoff LLP.

(57) ABSTRACT

One embodiment of the present system and method is directed to the identification of tissues within a vascular object by analyzing ultrasound data collected from the vascular object by non-invasive scans. By identifying and characterizing types of tissue from ultrasound data, an assessment can be made about the health condition of a patient without an invasive procedure. Other applications of the present system will also be appreciated including identifying other types of tissues.

25 Claims, 5 Drawing Sheets

NON-INVASIVE TISSUE CHARACTERIZATION SYSTEM AND METHOD

BACKGROUND

Ultrasonic imaging provides a useful tool in various areas of medical practice for determining the best type and course of treatment. Imaging of the coronary vessels of a patient by ultrasonic techniques can provide physicians with valuable information. For example, the image data may show the extent of a stenosis in a patient, reveal progression of disease, and help determine whether procedures such as angioplasty or atherectomy are indicated or whether more invasive procedures may be warranted.

In a typical invasive ultrasound imaging system, an ultrasound transducer is attached to the end of a catheter that is carefully maneuvered through a patient's body to a point of interest such as within a blood vessel. After data is collected, images of the blood vessel are reconstructed using well-known techniques and the images are visually analyzed by a cardiologist to assess the vessel components and plaque content. However, this procedure is invasive and may create potential health risks to the patient that are unnecessary.

The present invention provides a new and useful method and system of characterizing tissue from a non-invasive scan.

SUMMARY

In accordance with one embodiment, a system for determining plaque composition is provided. The system comprises an ultrasound system with a non-invasive probe for collecting ultrasound data that includes backscatter signals from a blood vessel. Signal analyzer logic analyzes the ultrasound signal data and determines one or more signal properties from the backscatter signals of the blood vessel. Correlation logic is configured to associate the one or more signal properties to pre-determined signal properties from different plaque components, and identifies components of the blood vessel based on the association.

BRIEF DESCRIPTION OF THE DRAWINGS

In the accompanying drawings which are incorporated in and constitute a part of the specification, embodiments of a system and method are illustrated, which, together with the detailed description given below, serve to describe the example of the embodiment of the system and method. It will be appreciated that the illustrated boundaries of elements (e.g. boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vise versa.

DETAILED DESCRIPTION OF ILLUSTRATED EMBODIMENTS

Figure 1:
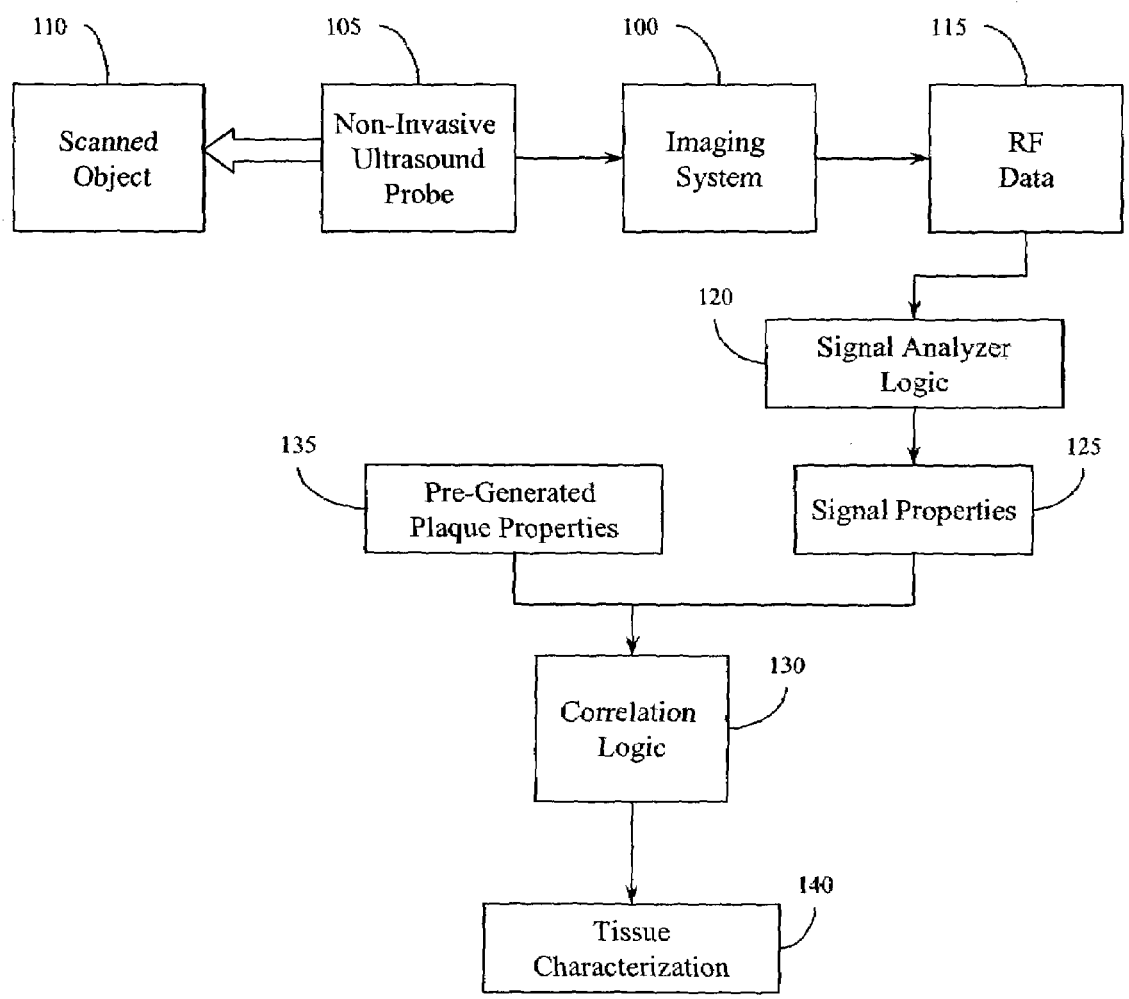
FIG. 1 is an example system diagram of one embodiment of an ultrasound analysis system for identifying tissue components.

The following includes definitions of selected terms used throughout the disclosure. Both singular and plural forms of all terms fall within each meaning:

"Computer-readable medium" as used herein refers to any medium that participates in directly or indirectly providing signals, instructions and/or data to one or more processors for execution. Such a medium may take many forms, including but not limited to, non-volatile media, volatile media, and transmission media. Non-volatile media may include, for example, optical or magnetic disks. Volatile media may include dynamic memory. Transmission media may include coaxial cables, copper wire, and fiber optic cables. Transmission media can also take the form of acoustic or light waves, such as those generated during radio-wave and infra-red data communications, or take the form of one or more groups of signals. Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, a PROM, an EPROM, a FLASH-EPROM, any other memory chip or cartridge, a carrier wave/pulse, or any other medium from which a computer, processor or other electronic device can read.

"Logic", as used herein, includes, but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), a programmed logic device, memory device containing instructions, or the like. Logic may also be fully embodied as software.

"Signal", as used herein, includes but is not limited to one or more electrical signals, analog or digital signals, one or more computer or processor instructions, messages, a bit or bit stream, or other means that can be received, transmitted, and/or detected.

"Software", as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in memory, part of an operating system or other type of executable instructions. It will be appreciated by one of ordinary skill in the art that the form of software is dependent on, for example, requirements of a desired application, the environment it runs on, and/or the desires of a designer/programmer or the like.

"User", as used herein, includes but is not limited to one or more persons, software, computers or other devices, or combinations of these.

In general, one embodiment of the present system and method is directed to the identification of plaques within a vascular object by analyzing ultrasound data collected from the human carotid artery by non-invasive scans. The carotid artery is the artery or pair of arteries that pass up a person's neck and supply blood to the head. By identifying and characterizing plaques from carotid ultrasound data, an assessment can be made as to a patient's risk of heart attack without an invasive procedure. The epidemiologic finding that cardiovascular and cerebrovascular morbidity are well correlated has led to the recognition of possible surrogates for the costly and sometimes invasive evaluation of the coronary circulation. An example of this is the carotid Intima-Media Thickness (IMT) measurement, which is now considered a "safe and non-invasive means of assessing subclinical atherosclerosis," by the American Heart Association Prevention Conference V.

However, measuring the IMT in a patient who has known plaque (and thus is no longer considered to have subclinical disease) may be of limited clinical use to determine future cardiovascular risk. This being the case, plaque volume and plaque characterization may evolve as better methods to predict cardiovascular events in years to come. Other applications of the present system will also be appreciated from the following descriptions.

Illustrated in FIG. 1 is one embodiment of an ultrasound imaging system configured to non-invasively scan an object and identify one or more components of the object. The system includes an ultrasound imaging system console 100 that includes data processing, analysis, and/or display capabilities. The imaging console 100 may be, for example, a General Electric Vivid 5 Echocardiography System, a Hewlett-Packard SONOS System, or other types of ultrasound systems. In another embodiment, the imaging console 100 may be a general purpose computer configured to communicate with and collect data from an ultrasound probe 105. In another embodiment, the console 100 may be a small portable scanner. The ultrasound probe 105 is a non-invasive ultrasonic device configured to scan an object 110 from a location external to a patient's body. The probe 105 includes one or more transducers that acquire radio frequency data from the scanned object 110. Various types of probes can be used, for example, a phased-array probe, a linear probe, a curvilinear probe or other types of hand-held probes.

In the following example, the system is configured to analyze ultrasound data collected from a scan of a carotid artery. To perform a scan, the ultrasound probe 105 would be placed against a person's neck near a region of interest. The transducers of the probe would be pulsed along scan lines and then acquire echoes of backscatter signals reflected from the tissue along each scan line. Different types and densities of tissue absorb and reflect the ultrasound pulses differently. Tissues that receive the pulsed signal reflect and transmit some of the pulse energy as a backscatter or reflected signal. The backscattered signals are then received by the transducer(s) in the probe 105. The difference between the signals transmitted and received by the probe 105 is that the received signal is the attenuated and backscattered version of the transmitted signal.

This backscatter signal is characteristic of the type of tissue that reflected it. Differences in the backscatter signal along each scan line can be determined by performing a frequency analysis on the signals. As a result, identifying different signal characteristics along each scan line allows for a correlation to the type of tissue associated with those particular signal characteristics. As will be described below, signal characteristics of the backscattered signal can serve as a signature for different types of components within an artery, including plaque components.

Figure 2:
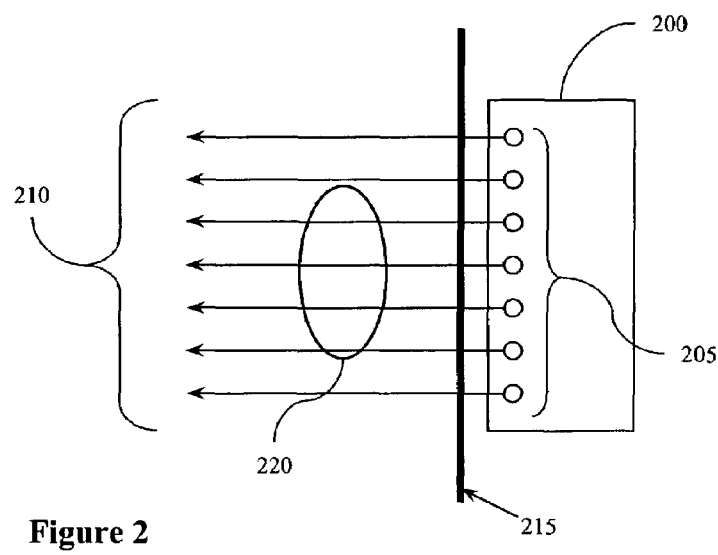
FIG. 2 illustrates one embodiment of a non-invasive ultrasound probe scanning an object.

Illustrated in FIG. 2 is a simplified diagram of one embodiment of an ultrasound probe 200 including a linear array of transducers 205. Depending on the type of probe, different numbers of transducers may be used, for example, 192 transducers. Transducers may pulse separately, or together creating a plurality of scan lines 210. Line 215 represents the skin of a patient and object 220 represents a cross-section view of a vascular object such as a carotid artery. By placing the probe 200 against a person's neck, ultrasound data can be collected from the carotid artery 220.

With reference again to FIG. 1, the data collected by the ultrasound probe 105 is initially in the form of raw radio frequency (RF) data 115 of the backscattered signals along each scan line. The RF data 115 is then analyzed to determine various signal characteristics that may identify associated tissue types. A signal analyzer logic 120 is configured to process and analyze the radio frequency data 115 to identify, in real-time, the vascular components of the scanned carotid artery. In this embodiment, the logic is configured to identify various types of plaque components and to provide an assessment as to the patient's condition based on the type of plaque identified, an amount of plaque component identified, or both.

In one embodiment, the signal analyzer logic 120 includes logic to transform the radio frequency data 115 to the frequency domain and analyze frequency information of the signals to determine one or more signal properties 125. For example, each scan line can be analyzed in segments and signal properties are determined for each segment. The segments may be equal in size, different in size, equally spaced from each other, overlapping each other, and/or defined in other desired ways.

Figure 3:
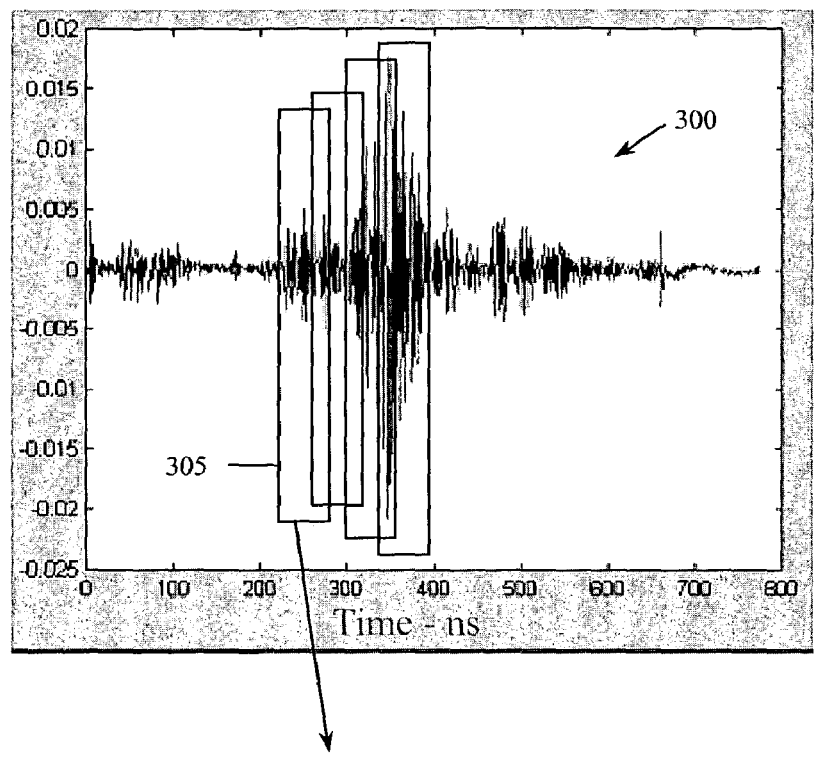
FIG. 3 illustrates one embodiment of an ultrasonic A-scan.
Figure 4:
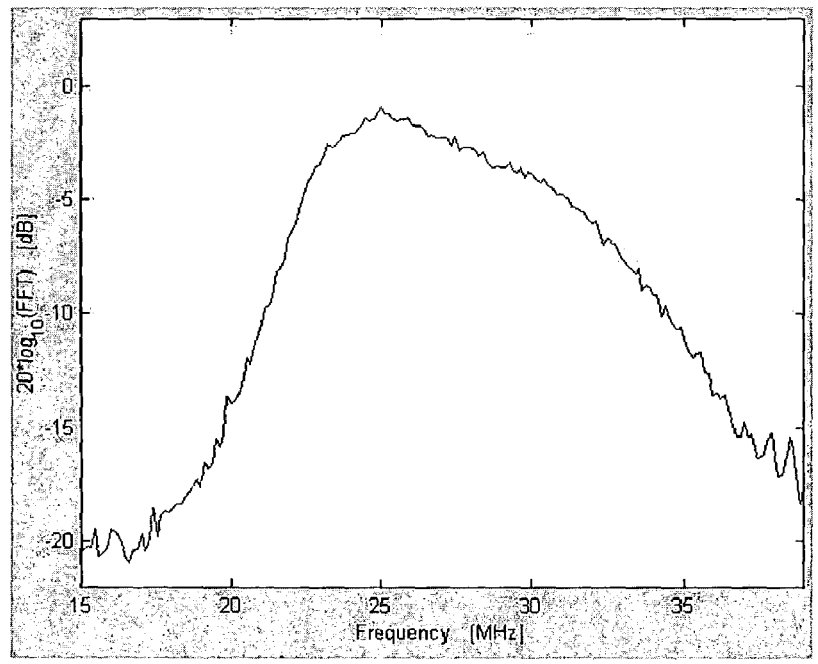
FIG. 4 illustrates one embodiment of a power spectrum plot generated from the A-scan signal of FIG. 3.

Illustrated in FIG. 3 is one example of radio frequency data of one scan line 300 plotted as voltage over time. The scan line can be analyzed in segments represented by the windows illustrated in the figure, such as window 305. The radio frequency data within the window 305 is transformed in this embodiment to a power spectrum density plot as shown in FIG. 4. Signal properties from the segment 305 are determined from the power spectrum of FIG. 4. Signal properties, in this case also referred to as spectral properties, may include the y-intercept, maximum power, mid-band fit, minimum power, frequencies at maximum and minimum powers, slope of regression line, integrated backscatter, or combinations of these or others.

With reference again to FIG. 1, the signal properties 125 are processed by a correlation logic 130 configured to correlate the signal properties of the scan line segment with the type of vascular component having those or similar signal properties. In that regard, the correlation logic 130 is configured to compare and match the signal properties 125 to pre-determined signal properties 135. In one embodiment, the pre-determined signal properties 135 are configured in a data structure that associates measured or observed signal properties to a type of vascular component such as normal tissue, the lumen, and types of plaque components that may be present. Various plaque components include, calcium, fibrous, fibrolipid, and calcified-necrosis. The data structure may be implemented in a variety of ways including a data file, an array, a table, a linked list, a tree structure, a database, combinations of these and multiple components of each if desired. The correlation logic 130 matches the signal properties 125 from a scan line, or a region of the scan line, to the pre-determined properties 135 and outputs a tissue characterization 140 that identifies the type of tissue. The system repeats the analysis for other segments on this scan line and for the other scan lines.

Once a sufficient amount of ultrasound data is analyzed and characterized, a diagnostic logic may be included to generate an assessment as to the type and amount of plaque identified and a health condition of the patient in terms of cardiovascular disease or other associated health problems. Additionally, the diagnostic logic may be configured to reconstruct the ultrasound data into displayed images and, the identified components can be visually distinguished on the display. Based on the assessment of plaque composition, the logic can be configured to generate a score indicating the health condition of a patient. For example, a score of zero may indicate no risk of heart attack while a score of ten may indicate a high risk of heart attack. With this score, a physician may recommend a particular treatment which may include monitoring, life-style changes, medication and/or surgery. The score may also be helpful to convince a patient of their condition.

Figure 5:
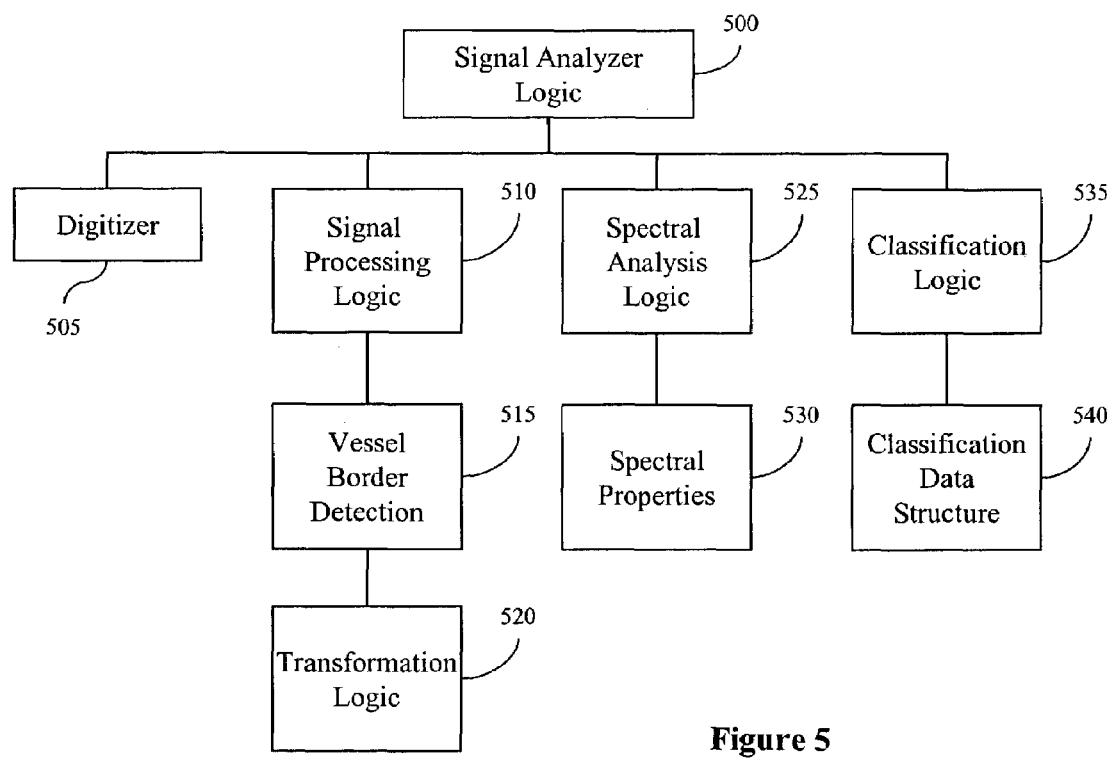
FIG. 5 is another embodiment of a signal analyzer system.

Illustrated in FIG. 5 is one embodiment of signal analyzer logic 500 for processing and analyzing radio frequency ultrasound data. It will be appreciated that the signal analyzer logic 500 may be embodied as part of an ultrasound imaging console or as part of a separate system that receives raw radio frequency data from an ultrasound console. If the radio frequency data is in analog form, a digitizer 505 may be provided to digitize the data. A signal processing logic 510 is configured to process each scan line of the ultrasound data and transform it to a format that can be analyzed. To reduce processing time, a border detection logic 515 may be used to determine the location of the borders of the vessel wall being scanned. Since the analysis is most interested in the components of the carotid artery, scan line data outside of the artery can be filtered and removed. One example of a border detection system is described in U.S. Pat. No. 6,381,350, entitled "Intravascular Ultrasonic Analysis Using Active Contour Method and System," which is incorporated herein by reference for all purposes.

After border detection, the scan line data is transformed. Of course, border detection can be performed after transformation. Transformation logic 520 is configured to transform the remaining scan line data into a format suitable for analysis. In general, the transformed format should match the same format used to build the pre-determined signal properties of the vascular component. In one embodiment, the transformation logic 520 transforms the data to a power spectrum plot of frequency versus power output as shown in FIG. 4. Various transformation algorithms include a Fourier transformation, Welch periodograms, and auto-regressive modeling. Other types of transformations can include transforming the data to wavelets that provide an image with frequency and time information. Another transformation includes using impedance, rather than frequency, which gives an image of acoustic impedance. In this format, different tissue components have different impedance properties that provide different signal reflections. In the following example, a power spectrum density plot is used from a Fourier transformation.

With further reference to FIG. 5, spectral analysis logic 525 analyzes the power spectrum of the scan line data to determine its spectral properties 530. As mentioned previously, spectral properties or parameters may include maximum power, frequency at the maximum power, minimum power, the frequency at the minimum power, the slope, y-intercept, mid-band fit, and integrated backscatter. The spectral parameters 530 are then inputted to a classification logic 535 that attempts to classify the spectral parameters associated to a particular scan line segment with previously measured spectral parameters from a known vascular component.

In one embodiment, a classification data structure 540 contains a statistical classification of measured or observed spectral properties associated with particular types of vascular components. The classification data structure 540, in one embodiment, is previously generated from laboratory studies that correlate intra-vascular ultrasound data analysis of tissue samples with their corresponding histology sections. One example of this process is described in U.S. Pat. No. 6,200,268 B1, entitled "Vascular Plaque Characterization," issued Mar. 13, 2001, which is incorporated herein by reference for all purposes.

Figure 6:
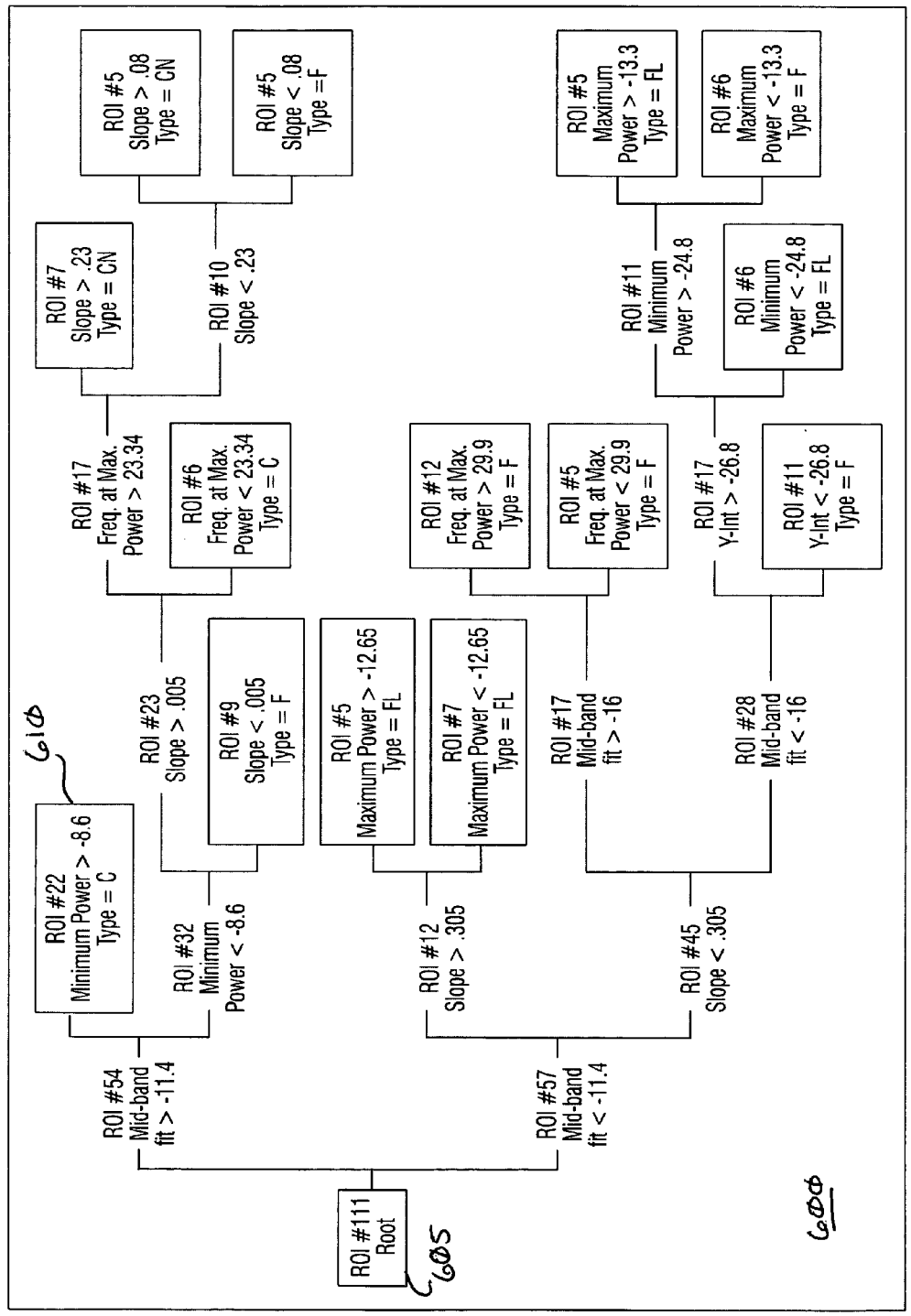
FIG. 6 shows one embodiment of a classification tree of spectral properties.

An example of a statistical classification tree 600 is shown in FIG. 6. The tree 600 may be based on a number of spectral properties measured from ultrasound data and matched to tissue components from corresponding histology samples. A variety of statistical software applications may be used to compile the data such as S Plus by Statistical Sciences, Inc., Seattle, Wash. The tree 600 includes a root node 605 that branches based on the signal properties compiled from the statistical algorithm. For example, the first branch level is based on a value of mid-band fit. The tree 600 terminates at leaf nodes (shown as boxes) that represent a particular type of tissue. In this example, the leaf nodes indicate tissue type C (calcified), type F (fibrous), type FL (fibro-lipidic) and type CN (calcified necrosis). Thus, by inputting a set of signal properties, the classification tree 600 can be traversed in accordance with the branching conditions and lead to a leaf node that identifies the type of tissue matching the inputted signal properties.

In a simple example, suppose spectral properties from one segment of a backscatter signal are determined to be: mid-band fit=−11.0 and minimum power=−8.2. Processing these properties through the classification tree 600 causes the tree to be traversed in two levels and end at a leaf node 610. Reaching leaf node 610 indicates that the segment corresponds to a Type=C (calcified) plaque. In this case, other spectral properties were not necessary to identify the tissue. This is because statistical data from the measured histology samples showed that some calcified plaque tissues had a mid-band fit>−11.4 and a minimum power>−8.6 as spectral properties. Of course, these are examples of spectral properties and the values may change based on the amount and type of data collected, the statistical algorithm used, or other factors that may effect the results.

Continuing the analysis for other segments of a backscatter signal and segments from other scan lines collected from a scan, the system can provide helpful identification of the types of components within the carotid artery. Additionally, based on the location of a segment along a scan line, the system can make a determination as to the location of the corresponding tissue within the carotid artery. Then by combining data from adjacent segments and adjacent scan lines having the same tissue component, the system can estimate the size and/or volume of the tissue component. This may be important because certain components may create a greater risk of plaque rupture and/or vessel occlusion based on their location and/or size and it would be helpful to identify these conditions.

Figure 7:
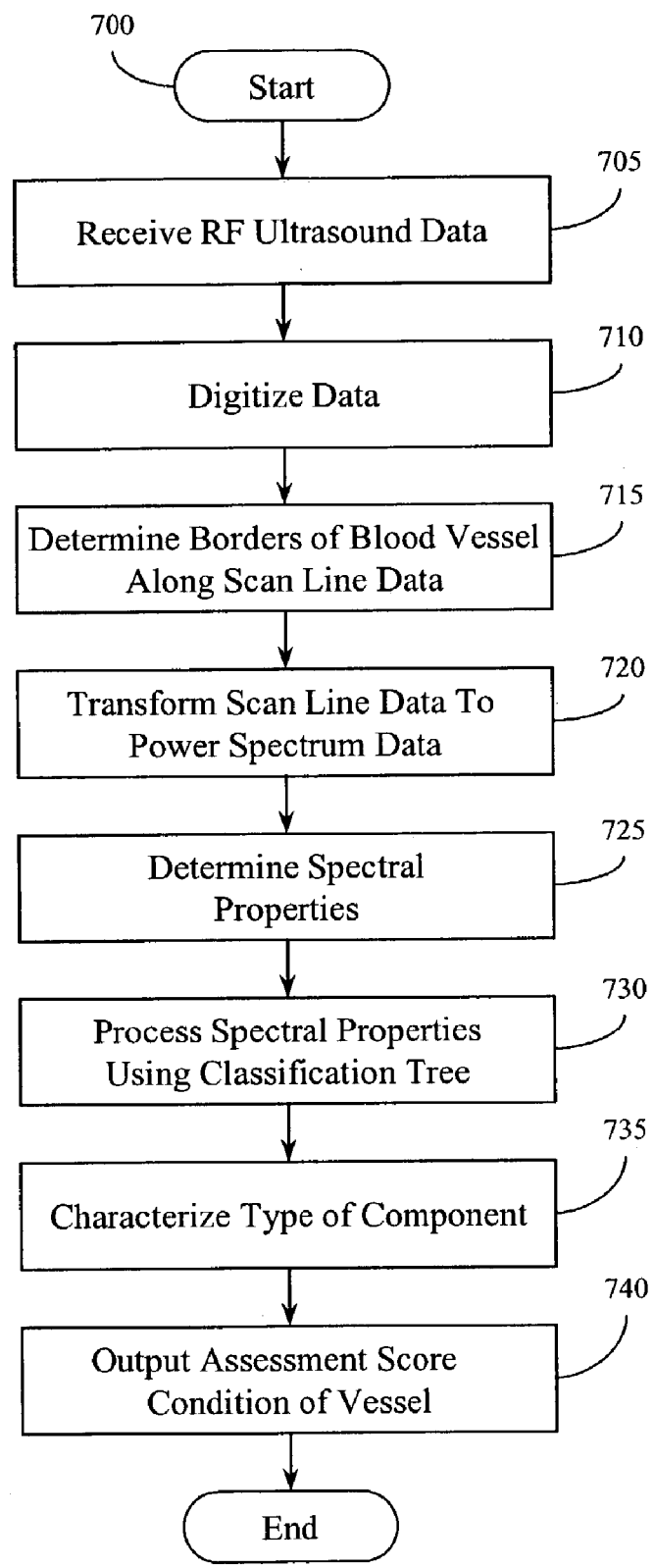
FIG. 7 is one embodiment of a methodology for identifying tissue components from an ultrasound scan.

Illustrated in FIG. 7 is one embodiment of a methodology 700 associated with analyzing ultrasound signals and identifying the type of component that corresponds to the signals. The illustrated elements denote "processing blocks" and represent computer software instructions or groups of instructions that cause a computer or processor to perform an action(s) and/or to make decisions. Alternatively, the processing blocks may represent functions and/or actions performed by functionally equivalent circuits such as a digital signal processor circuit, an application specific integrated circuit (ASIC), or other logic device. The diagram does not depict syntax of any particular programming language. Rather, the diagram illustrates functional information one skilled in the art could use to fabricate circuits, generate computer software, or use a combination of hardware and software to perform the illustrated processing. It will be appreciated that electronic and software applications may involve dynamic and flexible processes such that the illustrated blocks can be performed in other sequences different than the one shown and/or blocks may be combined or separated into multiple components. They may also be implemented using various programming approaches such as machine language, procedural, object-oriented, artificial intelligence, or other techniques. This applies to all methodologies described herein.

With reference to FIG. 7, analysis may begin as ultrasound data is received in real time during a scan or after a scan is completed (block 705). In this example, presume the region of interest for the scan is a vascular object such as a carotid artery. If the ultrasound data is still in the raw radio frequency form, it is digitized (block 710). In one embodiment, the digitized data is analyzed along a scan line, in one or more segments. The embodiment of FIG. 7 illustrates the analysis of one segment of data. Although not shown in FIG. 7, the processing repeats for each segment of a scan line and repeats for other scan lines until complete or until processing is stopped. Optionally, the process may allow for changing the properties of how a scan line is segmented such as defining various sizes and intervals of segments.

For a scan line being analyzed, a border detection algorithm may be used to identify the borders of the vascular object (block 715) and the analysis can be focused on the scan line data corresponding to the vascular object. Since the scan is not intravascular in this example, a scan line that passes through the vascular object may pass through two walls of the object. For example, FIG. 2 illustrates a number of scan lines 210 passing through two walls of a scanned object 215. Thus, the border detection would attempt to search and identify two borders along a scan line. Many different border detection methods are available including analyzing signal properties of the scan line, reconstructing an image from the ultrasound data and detecting borders from the image data, and other methods. Scan line data outside the borders of the vascular object may be ignored or removed from analysis if desired.

With reference again to FIG. 7, the scan line can be segmented and analyzed by segment. In one embodiment, the signal data from a segment is transformed to a power spectrum form (block 720) such as in FIG. 4. Spectral properties are determined from the power spectrum (block 725) which may include the y-intercept, maximum power, mid-band fit, minimum power, frequencies at maximum and minimum powers, slope of regression line, integrated backscatter, and/or other properties from the power spectrum. The spectral properties of the scan line data are then compared to pre-determined spectral properties of known vascular components to determine which type of component best matches the scan line spectral properties.

In one embodiment, the pre-determined spectral properties are structured as a classification tree generated from statistical analysis of how the properties correlate to a type of tissue component. An example of a tree structure is shown in FIG. 6, which includes branch nodes having conditions for spectral property values. The scan line spectral properties are then processed through the tree (block 730), traversing branches based on how the spectral properties meet the conditions of the branch nodes. The tree is traversed to a leaf node that identifies a type of tissue component. The spectral properties of the scan line segment are then characterized as this type of component (block 735).

The analysis continues for the other segments of the scan line and other scan lines. When a sufficient amount of scan line data has been characterized, an assessment can be generated and outputted reflecting a health condition of the patient and/or condition of the blood vessel (block 740). A diagnostic score and/or an image may also be generated indicating the health condition which may include a display of the type and amount of plaque identified, the location of the plaque, the potential risk of heart attack, or other conditions. By determining the condition of the carotid artery through a non-invasive scan, an assessment can be made as to a patient's cardiovascular condition. A presumption made is that there is a correlation between the condition of the carotid arteries and the condition of the coronary arteries. If the carotid arteries show certain levels of plaque, it can be presumed that similar conditions may exist in the coronaries. Other factors may also be used to provide a diagnosis such as a patient's medical history, family medical history, and other factors. An appropriate treatment may then be prescribed. Scanning the carotid arteries allows for a diagnosis without having to perform an invasive procedure that may expose a patient to the risks associated with surgery.

In another embodiment, the system can be configured to identify tissue from an external breast scan. For example, scanning an unknown lump within a breast and determining whether it may be cancerous can serve as an early diagnostic tool. In this embodiment, pre-determined correlations between ultrasound signal properties and cancerous and non-cancerous tissue would be obtained and stored in a data structure. The correlations can be obtained in a similar manner as those described above for vascular objects. This may include collecting ultrasound signal data from physical samples of tissue and matching the data with corresponding tissue from a histology sample of the tissue.

One embodiment can be implemented similar to the system of FIG. 1 except that the pre-determined plaque properties 135 would be substituted with a data structure including signal properties of cancerous tissue, non-cancerous tissue, or both. One form of the structure may be a statistical classification tree. To perform a scan, a non-invasive probe would be positioned against the tissue of a breast near a region of interest (e.g. a suspected lump). The ultrasound data would then be analyzed to determine spectral properties or other signal properties in a similar manner as described previously. If the spectral properties sufficiently match pre-determined spectral properties of cancerous tissue, the system can output a signal indicating that cancerous tissue may be present. Since the type of cancerous tissue is not as important for this type of early diagnosis, a simple yes or no can be the output. It will be appreciated that the system can be configured to identify any desired type of tissue or object using the techniques discussed here.

Suitable software for implementing the various components of the present system and method using the teachings presented here include programming languages and tools such as Java, Pascal, C#, C++, C, CGI, Perl, SQL, APIs, SDKs, assembly, firmware, microcode, and/or other languages and tools. The components embodied as software include readable/executable instructions that cause one or more computers, processors and/or other electronic device to behave in a prescribed manner. Any software, whether an entire system or a component of a system, may be embodied as an article of manufacture and maintained as part of a computer-readable medium as defined previously. Another form of the software may include signals that transmit program code of the software to a recipient over a network or other communication medium. It will be appreciated that components described herein may be implemented as separate components or may be combined together.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. A system for determining plaque composition, the system comprising:
   an ultrasound system with a non-invasive probe for collecting ultrasound data including backscatter signals from a blood vessel;
   a signal analyzer for analyzing the ultrasound signal data and determining one or more signal properties from the backscatter signals of the blood vessel; and
   a correlation processor configured to associate the one or more signal properties to pre-determined signal properties of plaque components wherein the pre-determined signal properties are embodied as a classification tree having branch node conditions based on the pre-determined signal properties and one or more leaf nodes that identify a type of plaque component, the correlation processor further configured to identify a plaque component based on the one or more signal properties.

2. The system of claim 1 further including transformation logic configured to transform the ultrasound data to a power spectral density format.

3. The system of claim 2 wherein the one or more signal properties includes one or more spectral properties.

4. The system of claim 1 wherein the correlation processor being configured to traverse the classification tree to a leaf node based on a comparison of the one or more signal properties from the backscatter signal to the branch node conditions.

5. The system of claim 1 further including border detection logic configured to determine borders of the blood vessel from the backscatter signals.

6. The system as set forth in claim 5, where the signal analyzer logic selectively analyzes substantially only the ultrasound signal data within the borders of the blood vessel.

7. The system of claim 1 wherein the non-invasive probe is configured to collect the ultrasound data with a plurality of transducers.

8. The system of claim 1 wherein the ultrasound system includes at least one processor configured to process the ultrasound data.

9. The system of claim 1 wherein the ultrasound system further includes diagnostic logic for generating an assessment as to a health condition based on the components of the blood vessel identified.

10. An article of manufacture embodied in a computer-readable medium for use in a processing system for analyzing ultrasound signal data, the article of manufacture comprising:
    first processor executable instructions for causing a processor to receive ultrasound signal data of a scanned object collected from a non-invasive probe;
    second processor executable instructions for causing a processor to determine signal properties of one or more regions of interest associated with the scanned object from the ultrasound signal data; and
    third processor executable instructions for causing a processor to classify the one or more regions of interest as a component type based on a classification data structure pre-determined from measured associations between signal properties and one or more component types of an object similar to the scanned object, the classification data structure having branch node conditions and one or more leaf nodes that identify the component based on the measured associations.

11. The article of manufacture as set forth in claim 10 further including fourth processor executable instructions for causing a processor to generate an assessment relating to a condition of the scanned object based on the classified one or more regions of interest.

12. The article of manufacture as set forth in claim 11 wherein the assessment is a score reflecting an amount of a plaque component identified within the scanned object.

13. The article of manufacture as set forth in claim 11 wherein the assessment is an image identifying the classified regions of interest.

14. The article of manufacture as set forth in claim 10 further including fourth processor executable instructions for causing a processor to analyze a frequency spectrum of the ultrasound signal data where the signal properties include spectral properties.

15. The article of manufacture as set forth in claim 10 wherein the non-invasive probe is configured to scan an object from a location external to the object.

16. The article of manufacture as set forth in claim 10 wherein the second processor executable instructions include instructions for causing a processor to analyze frequency data from the ultrasound signal data to determine the signal properties of the one or more regions of interest.

17. The article of manufacture as set forth in claim 10 wherein the ultrasound signal data includes a plurality of scan line data and, the second processor executable instructions include instructions for causing a processor to segment the scan line data.

18. The article of manufacture as set forth in claim 10 wherein the classification data structure includes measured associations between signal properties and one or more component types of cancerous and non-cancerous tissue.

19. The article of manufacture as set forth in claim 10 wherein the classification data structure includes measured associations between signal properties and one or more component types of plaque.

20. A method of identifying one or more components of an object, the method comprising:
    receiving backscatter signals from an ultrasonic probe scanning the object from a location external to the object;
    determining one or more signal properties from the backscatter signals;
    associating the one or more signal properties to pre-determined signal properties of object components wherein the pre-determined signal properties comprise branch node conditions based on the pre-determined signal properties and one or more leaf nodes identifying a type of object component; and identifying one or more object components based on the associating.

21. The method as set forth in claim 20 wherein the backscatter signals include a plurality of scan lines and the determining step includes determining signal properties for a plurality of segments from the plurality of scan lines.

22. The method as set forth in claim 20 where the receiving step includes collecting backscatter signals from a carotid artery.

23. The method as set forth in claim 22 where the identifying step includes identifying one or more types of plaque within the carotid artery.

24. The method as set forth in claim 20 where the receiving step includes collecting backscatter signals from breast tissue.

25. The method as set forth in claim 24 where the identifying step includes identifying whether cancerous tissue is present.

* * * * *